US011568832B2

(12) United States Patent
Mittal et al.

(10) Patent No.: US 11,568,832 B2
(45) Date of Patent: Jan. 31, 2023

(54) SYSTEM AND METHOD FOR OCULAR ASSISTANCE

(71) Applicant: IPexcel Services Pvt. Ltd., Bangalore (IN)

(72) Inventors: Pranjal Mittal, New Delhi (IN); Amit Mendiratta, New Delhi (IN); Rishi Verma, Bengaluru (IN); Vidya Bhaskar Singh Nandiyal, Bangalore (IN)

(73) Assignee: IPexcel Services Pvt. Ltd.

( * ) Notice: Subject to any disclaimer, the term of this patent is extended or adjusted under 35 U.S.C. 154(b) by 0 days.

(21) Appl. No.: 17/409,337

(22) Filed: Aug. 23, 2021

(65) Prior Publication Data
US 2022/0059048 A1    Feb. 24, 2022

(30) Foreign Application Priority Data

Aug. 23, 2020    (IN) .............................. 202041012626

(51) Int. Cl.
*A61B 3/06* (2006.01)
*A61B 3/036* (2006.01)
*G09G 5/02* (2006.01)

(52) U.S. Cl.
CPC .............. *G09G 5/02* (2013.01); *A61B 3/036* (2013.01); *A61B 3/066* (2013.01); *G09G 2320/0666* (2013.01); *G09G 2354/00* (2013.01)

(58) Field of Classification Search
None
See application file for complete search history.

(56) References Cited

U.S. PATENT DOCUMENTS

2013/0027420 A1* 1/2013 Felt .................. G09G 5/028
                                                        345/594
2016/0035063 A1* 2/2016 Mese ................ G06F 3/04847
                                                        345/660
(Continued)

FOREIGN PATENT DOCUMENTS

EP    1646310 B1    7/2015
EP    3195091 A1    7/2017
(Continued)

OTHER PUBLICATIONS

John Brennan; What Is the Maximum Magnification of the Human Eye?; Apr. 25, 2017; https://sciencing.com/maximum-magnification-human-eye-6622019.html.

*Primary Examiner* — Kyle Zhai
(74) *Attorney, Agent, or Firm* — Jason C. Cameron

(57) ABSTRACT

A system for ocular assistance is disclosed. The plurality of subsystem includes an ocular condition registration subsystem, configured to register one or more users. The plurality of subsystem includes an ocular calibration subsystem, configured to determine a plurality of ocular settings. The plurality of subsystem includes a device configuration identification subsystem, configured to determine a plurality of device settings for each of one or more device associated with the registered one or more users. The plurality of subsystem includes a screen customization subsystem, configured to determine values corresponding to the plurality of ocular settings based on a pre-stored look up table and determined plurality of device settings. The screen customization subsystem modifies current values corresponding to the plurality of ocular settings to the determined values. The system modifies or rectifies the screen images or texts for suffering users.

8 Claims, 4 Drawing Sheets

(56) References Cited

U.S. PATENT DOCUMENTS

| | | |
|---|---|---|
| 2017/0119298 A1 | 5/2017 | Cheung |
| 2019/0056780 A1* | 2/2019 | Bombard .............. G06T 19/006 |
| 2021/0034147 A1* | 2/2021 | Gadge .................. G09B 21/008 |

FOREIGN PATENT DOCUMENTS

| | | |
|---|---|---|
| EP | 3532892 A1 | 9/2019 |
| WO | 2018113680 A1 | 6/2018 |

* cited by examiner

SYSTEM AND METHOD FOR OCULAR ASSISTANCE

EARLIEST PRIORITY DATE

This application claims priority from a Provisional patent application filed in India having Patent Application No. 202041012626, filed on Aug. 23, 2020 and titled "SYSTEM AND METHOD FOR OCULAR ASSISTANCE".

FIELD OF INVENTION

Embodiments of the present disclosure relates to the field of vision correction systems, and more particularly to a system and a method for ocular assistance corresponding to digital displays.

BACKGROUND

In order to clearly view text and images, individuals use reading glasses, prescription eyewear, including contact lenses, or other types of corrective eyewear. This includes text and images displayed on display of a device, such as a screen of a computer monitor or a handheld mobile device.

However, in certain scenario, the individual may not wear a correct eyewear. The individual may perceive the images displayed on the device to be blurry without correction to focal length provided by their corrective eyewear.

To cope with the above problem, existing solutions use a dedicated application for magnification of an area on the display. The said solution can be used by the individuals suffering from far-sightedness. Further, for the individuals suffering from a partial colour blindness or any other form of eye defect, the existing solutions replace colours which affect the individual's vision by other colours in order to rectify the partial colour blindness of the individuals.

Furthermore, wearing a spectacle or contact lens for a longer duration often tends to bring an overhead for the individual. Also, user experience gets further degraded, if the individual who is consuming a visual content is colour blind. An effective system is needed to solve all types of problems concerning ocular conditions in real time.

Hence, there is a need for an improved system for ocular assistance related to digital displays and a method to operate the same and therefore address the aforementioned issues.

BRIEF DESCRIPTION

In accordance with one embodiment of the disclosure, a system for ocular assistance is disclosed. The system includes a hardware processor. The system also includes a memory coupled to the hardware processor. The memory comprises a set of program instructions in the form of a plurality of subsystems, configured to be executed by the hardware processor.

The plurality of subsystems includes an ocular condition registration subsystem. The ocular condition registration subsystem is configured to register one or more users with corresponding ocular condition details. The plurality of subsystems also includes an ocular calibration subsystem. The ocular calibration subsystem is configured to determine a plurality of ocular settings required for each of registered one or more users.

The plurality of subsystems also includes a device configuration identification subsystem. The device configuration identification subsystem is configured to determine a plurality of device settings for each of one or more device associated with the registered one or more users.

The plurality of subsystem also includes a screen customization subsystem. The screen customization subsystem is configured to determine values corresponding to the plurality of ocular settings based on a pre-stored look up table and determined plurality of device settings.

The screen customization subsystem is also configured to modify current values corresponding to the plurality of ocular settings to the determined values corresponding to the plurality of ocular settings. The screen customization subsystem is also configured to render the one or more display screens with the modified current values.

In accordance with one embodiment of the disclosure, a method for implementation of ocular assistance. The method includes registering one or more users with corresponding ocular condition details. The method also includes determining a plurality of ocular settings required for each of registered one or more users.

The method also includes determining a plurality of device settings for each of one or more device associated with the registered one or more users. The method also includes determining values corresponding to the plurality of ocular settings based on a pre-stored look up table and determined plurality of device settings.

The method also includes modifying current values corresponding to the plurality of ocular settings to the determined values corresponding to the plurality of ocular settings. The method also includes rendering the one or more display screens with the modified current values.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Figure 1:
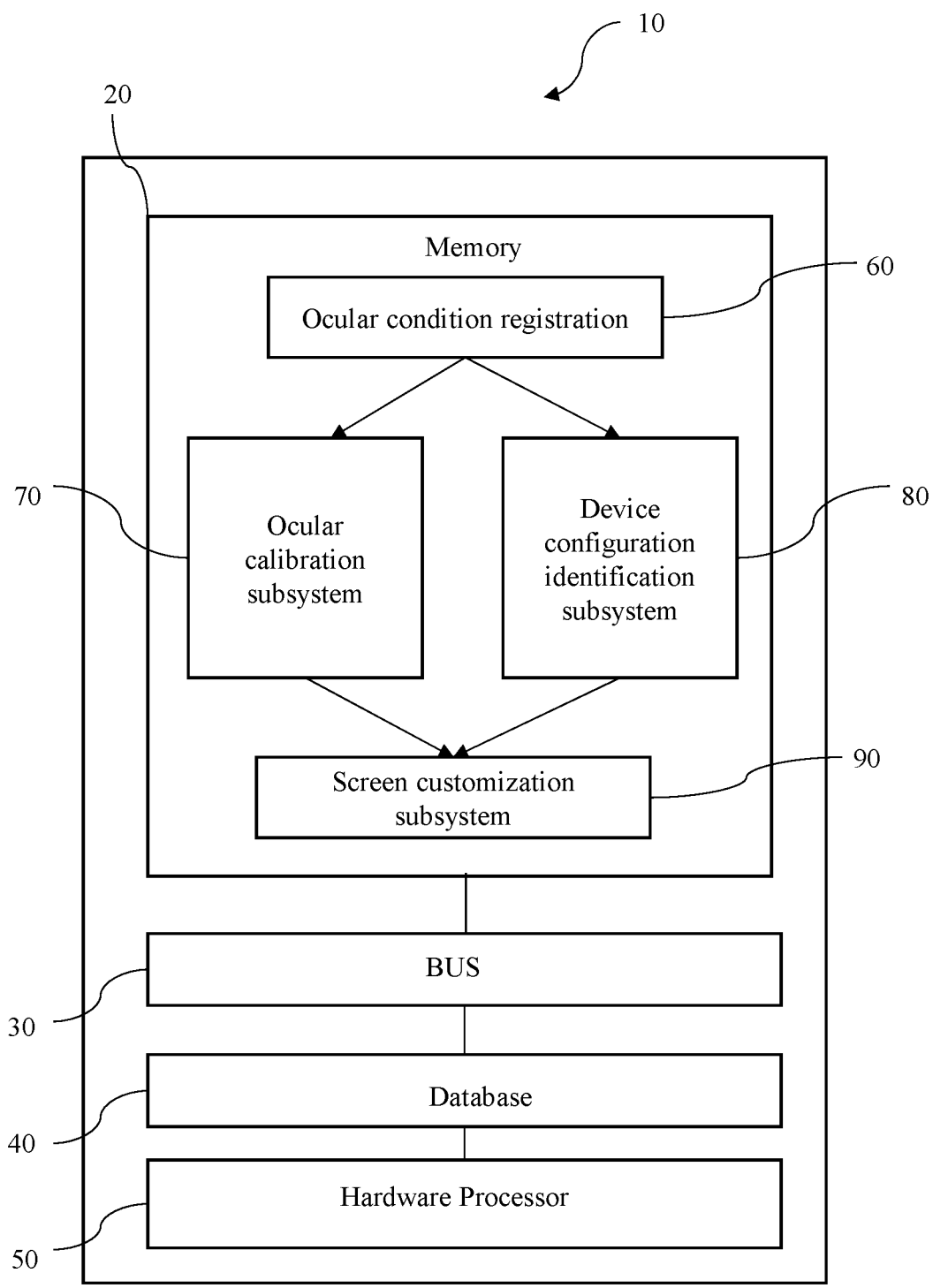
FIG. 1 is a block diagram illustrating various components of an exemplary computing system for ocular assistance in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated online platform, and such further applications of the principles of the disclosure as would normally occur to those skilled in the art are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or subsystems or elements or structures or components preceded by "comprises . . . a" does not, without more constraints, preclude the existence of other devices, subsystems, elements, structures, components, additional devices, additional subsystems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

A computer system (standalone, client or server computer system) configured by an application may constitute a "subsystem" that is configured and operated to perform certain operations. In one embodiment, the "subsystem" may be implemented mechanically or electronically, so a subsystem may comprise dedicated circuitry or logic that is permanently configured (within a special-purpose processor) to perform certain operations. In another embodiment, a "subsystem" may also comprise programmable logic or circuitry (as encompassed within a general-purpose processor or other programmable processor) that is temporarily configured by software to perform certain operations.

Accordingly, the term "subsystem" should be understood to encompass a tangible entity, be that an entity that is physically constructed permanently configured (hardwired) or temporarily configured (programmed) to operate in a certain manner and/or to perform certain operations described herein.

FIG. 1 is a block diagram illustrating various components of an exemplary computing system 10 for ocular assistance in accordance with an embodiment of the present disclosure The computing system 10 assists one or more users with different eye defects to view a computer display screen and enjoy smooth viewing experience.

The computing system 10 includes a hardware processor 50. The computing system 10 also includes a memory 20 coupled to the hardware processor 50. The memory comprises a set of program instructions in the form of a plurality of subsystems, configured to be executed by the hardware processor 50.

The hardware processor(s) 50, as used herein, means any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a digital signal processor, or any other type of processing circuit, or a combination thereof.

The memory 20 includes a plurality of subsystems stored in the form of executable program which instructs the processor via bus to perform the method steps described below. The plurality of subsystems includes: an ocular condition registration 60, an ocular calibration subsystem 70, a device configuration identification subsystem 80 and a screen customization subsystem 90.

Computer memory elements may include any suitable memory device(s) for storing data and executable program, such as read only memory, random access memory, erasable programmable read only memory, electrically erasable programmable read only memory, hard drive, removable media drive for handling memory cards and the like. Embodiments of the present subject matter may be implemented in conjunction with program modules, including functions, procedures, data structures, and application programs, for performing tasks, or defining abstract data types or low-level hardware contexts. Executable program stored on any of the above-mentioned storage media may be executable by the hardware processor(s) 50.

The ocular condition registration subsystem 60 is configured to register the one or more users with corresponding ocular condition details. The ocular condition details correspond to oculus sinister or left eye and oculus dextrus or right eye. In one embodiment, the ocular condition details comprise information associated with at least one of degree of myopia, degree of hyperopia, degree of astigmatism, degree of presbyopia, and colour blindness.

The degree of the plurality of ocular conditions is represented by Diopter "D", a unit used to measure the correction, or focusing power, of the lens. In such embodiment, the plurality of ocular conditions varies with different viewers and at times left eye of a viewer may have a different ocular condition than a right eye or there may be a variance in degree for the same ocular condition.

The astigmatism is a common vision condition that causes blurred vision. The astigmatism occurs when cornea (clear front cover of the eye) is irregularly shaped or sometimes because of curvature of the lens inside the eye (American Optometric Association). The viewers suffering with the astigmatism are provided with three numbers in their medical prescription. A general form for writing these numbers are S×C×Axis. The 'S' refers to a "spherical" portion of the medical prescription, which is the degree of near-sightedness or farsightedness. The 'C' refers to a "cylinder" or astigmatism and can be a negative or a positive number. The 'C' is also measured in dioptres the degree of astigmatism, where higher number dioptres denotes more astigmatism.

In one embodiment, the ocular condition registration subsystem 60 is configured to receive ocular condition details associated with the plurality of ocular conditions by way of manual input from each of the registered one or more users. The one or more users also input other personal details such as age, gender, eye defect history and the like.

In another embodiment, the ocular condition registration subsystem 60 is configured to receive ocular condition details associated with the plurality of ocular conditions by scanning of the medical prescription. In such an embodiment, the ocular condition registration subsystem 60 is configured to extract at least one of texts and numerals or combination thereof provided in the medical prescription. Further, the ocular condition registration subsystem 60 is also configured to correlate and understand type of ocular conditions and degrees by way of an optical character recognition (OCR) technology or any other known means.

In yet another embodiment, the ocular condition registration subsystem 60 is configured to receive ocular condition details associated with the plurality of ocular condition from a device such as a head mounted device. In such an embodiment, the ocular condition registration subsystem 60 is communicatively coupled to the head mounted device. Further, the head mounted device is adapted to be worn over the head of any user and capture the details associated with the ocular condition of the user and communicate the captured details associated with the ocular condition of the user to the ocular condition registration subsystem 60.

In an alternative embodiment, where the user does not have the medical prescription and also does not have access to any head mounted device, the ocular condition registration subsystem 60 is configured to render and display a plurality of three dimensional (3D) images or text at different depths of the display screen to the user. The ocular condition registration subsystem 60 may also simultaneously display the 3D images or text at different depths in different areas of the display screen to identify values of the "S" or "C". In such an embodiment, the user is enabled to select one or more images or texts at varying depth(s) according to his/her comfort. The selected images or texts are analysed to infer and generate the medical prescription for the user.

In another specific embodiment, the ocular condition registration subsystem 60 is configured to receive ocular condition details from Electronic Health Record (EHR) of the one or more users. As used herein, the term "electronic health record" refers to the systematized collection of patient electronically stored health information in a digital format.

The plurality of subsystems also includes an ocular calibration subsystem 70. The ocular calibration subsystem 70 is configured to determine a plurality of ocular settings required for each of the registered one or more users. In one embodiment, the plurality of ocular settings comprises display screen settings such as pixel size, zoom factor, scale factor, screen resolution, saturation level, contrast level, brightness level, icon arrangement and the like.

In one exemplary embodiment, for determining the zoom factor, zoom focal length is calculated from the formula $f=D/d_0$ multiplied by $f_h$. In such embodiment, $d_0$ is a default zoom distance at which the object will appear and $f_h$ is the focal length of the user's (human) optical system. Th object focused on by the viewer is positioned at the distance D.

The plurality of ocular settings are determined based on registered user profiles. For example, if a registered user has myopic defect, then the plurality of ocular settings corresponding to that eye defect is determined using prestored lookup table. The prestored lookup table comprises eye defects and corresponding ocular settings. Each eye defect may have different ocular settings. The prestored lookup table may also be generated using any artificial intelligence-based methods.

The plurality of subsystems further includes a profile generation subsystem. The profile generation subsystem is configured to generate a profile for each of the registered one or more users based on average distance maintained by each of the registered one or more users with respect to the display screen, variations in the distance maintained by each of the registered one or more users in comparison with a predefined distance most suitable for reading. In such embodiment, some other factors include position of head, posture of each of the registered one or more users, ocular condition of the each of the registered one or more users and the computed corrective calibration for each of the registered one or more users.

In another embodiment, the profile generation subsystem may also be configured to notify any aberration in posture of each of the registered one or more users and distance from the display screen with respect to an ideal distance for reading or viewing. In yet another embodiment, the profile generation subsystem may further be configured to recommend or suggest a posture for each of the registered one or more users.

The plurality of subsystems further includes a colour detection and annotation subsystem. The colour detection and annotation subsystem is configured to determine if the ocular settings correspond to a colour blindness. Furthermore, the colour detection and annotation subsystem is also configured to identify and annotate one or more colours present in the one or more images or texts displayed on the display screen. This is very helpful to the viewers who are colour blind or partially colour blind.

The plurality of subsystems also includes a device configuration identification subsystem 80. The device configuration identification subsystem 80 is configured to determine a plurality of device settings for each of one or more devices associated with the registered one or more users. In one embodiment, the one or more devices comprises any portable devices such as a handheld mobile, a laptop, a desktop, a head-mounted display device or a smart watch. The device settings comprise device type, device model, display screen dimensions, type of operating systems (OS) and the like. The device settings may be determined by retrieving system configuration files associated with the one or more devices.

The plurality of subsystem also includes a screen customization subsystem 90. The screen customization subsystem 90 is configured to determine values corresponding to the plurality of ocular settings based on a pre-stored look up table and determined plurality of device settings. The pre-stored lookup table comprises values of the plurality of ocular settings mapped to the determined eye defect or ocular condition. In one embodiment, the pre-stored look up table is created based on the profile generated by the profile generation subsystem. For example, for a user with myopia, the ocular settings that should be changed may be scale factor, and zoom factor. In such a case, the values corresponding to the scale factor and zoom factor are determined from the prestored lookup table.

The screen customization subsystem 90 is also configured to modify current values corresponding to the plurality of ocular settings to the determined values corresponding to the plurality of ocular settings. The screen customization subsystem 90 is also configured to render the one or more display screens with the modified current values. The modified values helps in customized screen settings that is best suitable for the registered one or more users.

Figure 2:
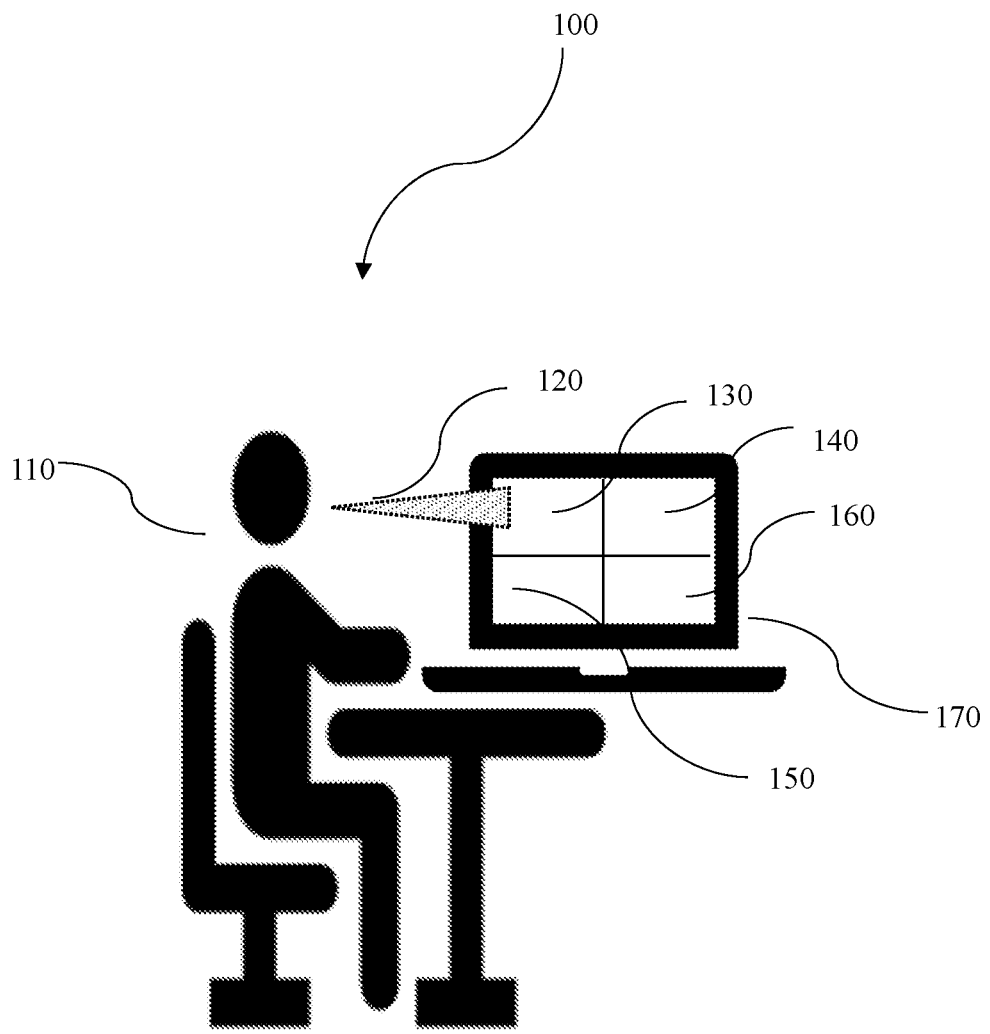
FIG. 2 depicts an illustration of a methodology of ocular assistance in accordance with an embodiment of the present disclosure.

FIG. 2 depicts an illustration of a methodology of ocular assistance 170 in accordance with an embodiment of the present disclosure The display screen 170 is divided into four parts 130,140,150 and 160. An eye gaze direction 120 of the viewer 110 is pointed towards apart 130 of the display screen 170. In this case, the calibration computing subsystem 80 computes corrective calibration for the part 130. This is helpful in scenarios where the images or texts being displayed after magnification goes beyond confines of the display screen 170 and is not correctly displayed. In specific embodiment, only the part of the display screen 170 where the viewer is gazing is rectified or modified. The magnification is given by the equation $M=-L'/L$, where L is the distance to the object and L' is the distance from the lens to the image it forms. L' for the human eye is always 1.7 cm.

Figure 3:
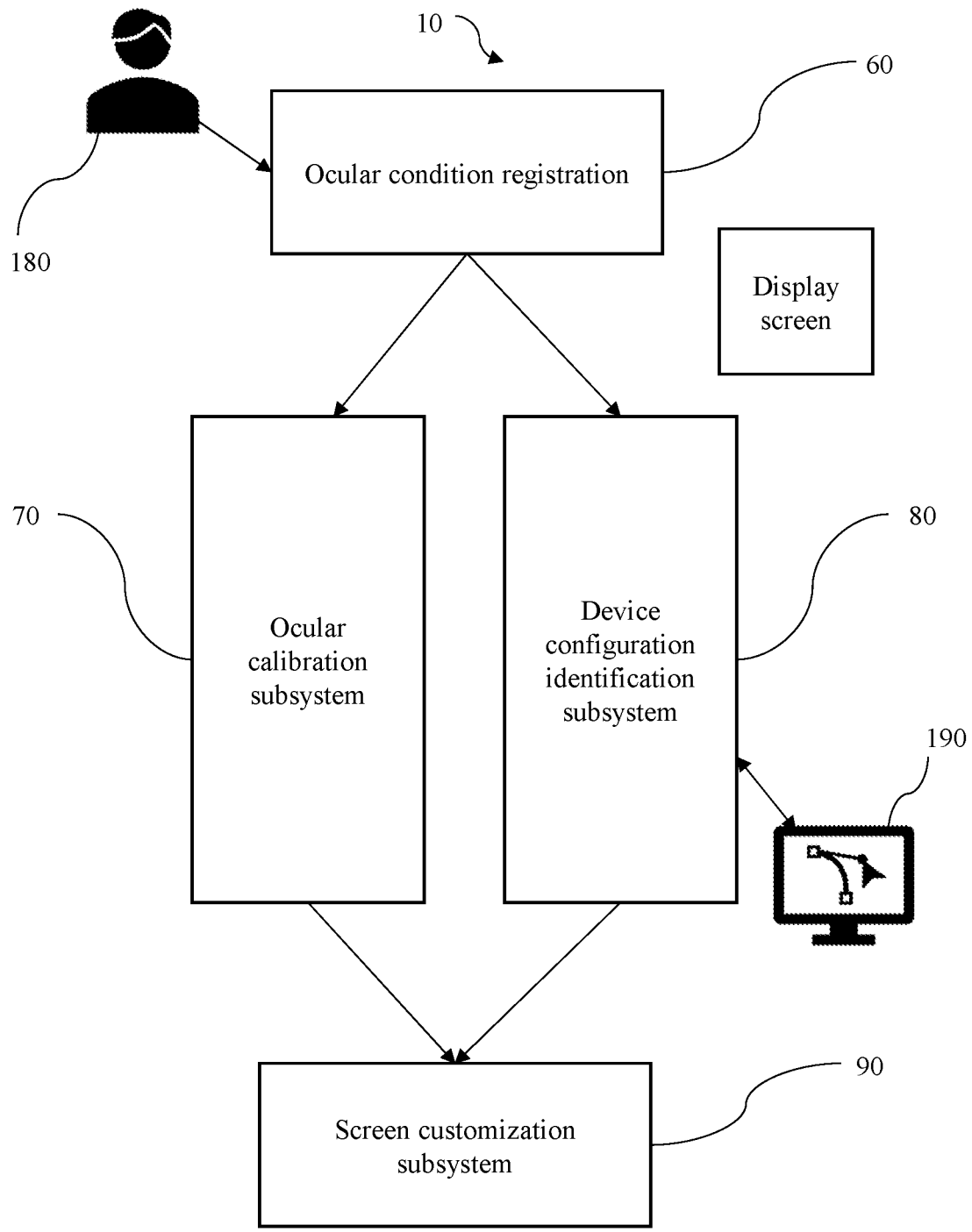
FIG. 3 is a block diagram illustrating an exemplary computing system for ocular assistance in accordance with another embodiment of the present disclosure.

FIG. 3 is a block diagram illustrating an exemplary computing system for ocular assistance in accordance with another embodiment of the present disclosure. In such exemplary embodiment, a user X 180 suffering from myopia inputs ocular condition details into the system 10 via an ocular condition registration subsystem 60. The ocular condition details comprise the Dioptre details of the left eye and the right eye. In such embodiment, the user X 180 is also registered in the computing system 10.

Correspondingly, an ocular calibration subsystem 70 determines the plurality of ocular settings required for each of registered one or more users. In such embodiment, the ocular calibration subsystem 70 determines what are the screen settings required on text or images for proper view by the user X 180.

The screen settings also depend on device Y 190 configuration. The device configuration identification subsystem 80 is configured to determine a plurality of device settings for device Y 190 associated with the user X 180.

Furthermore, the screen customization subsystem 90 is configured to determine values corresponding to the plurality of ocular settings based on a pre-stored look up table and determined plurality of device settings of the device Y 190. After determination, current values corresponding to the plurality of ocular settings is modified to the determined values corresponding to the plurality of ocular settings.

The screen customization subsystem 90 renders the display screen of the device Y 190 with the modified current values. The user X 180 may therefore view the customize screen without any viewing difficulty.

The ocular condition registration subsystem 60, the ocular calibration subsystem 70, the device configuration identification subsystem 80 and the screen customization subsystem 90 in FIG. 3 is substantially equivalent to the ocular condition registration subsystem 60, the ocular calibration subsystem 70, the device configuration identification subsystem 80 and the screen customization subsystem 90 of FIG. 1.

Figure 4:
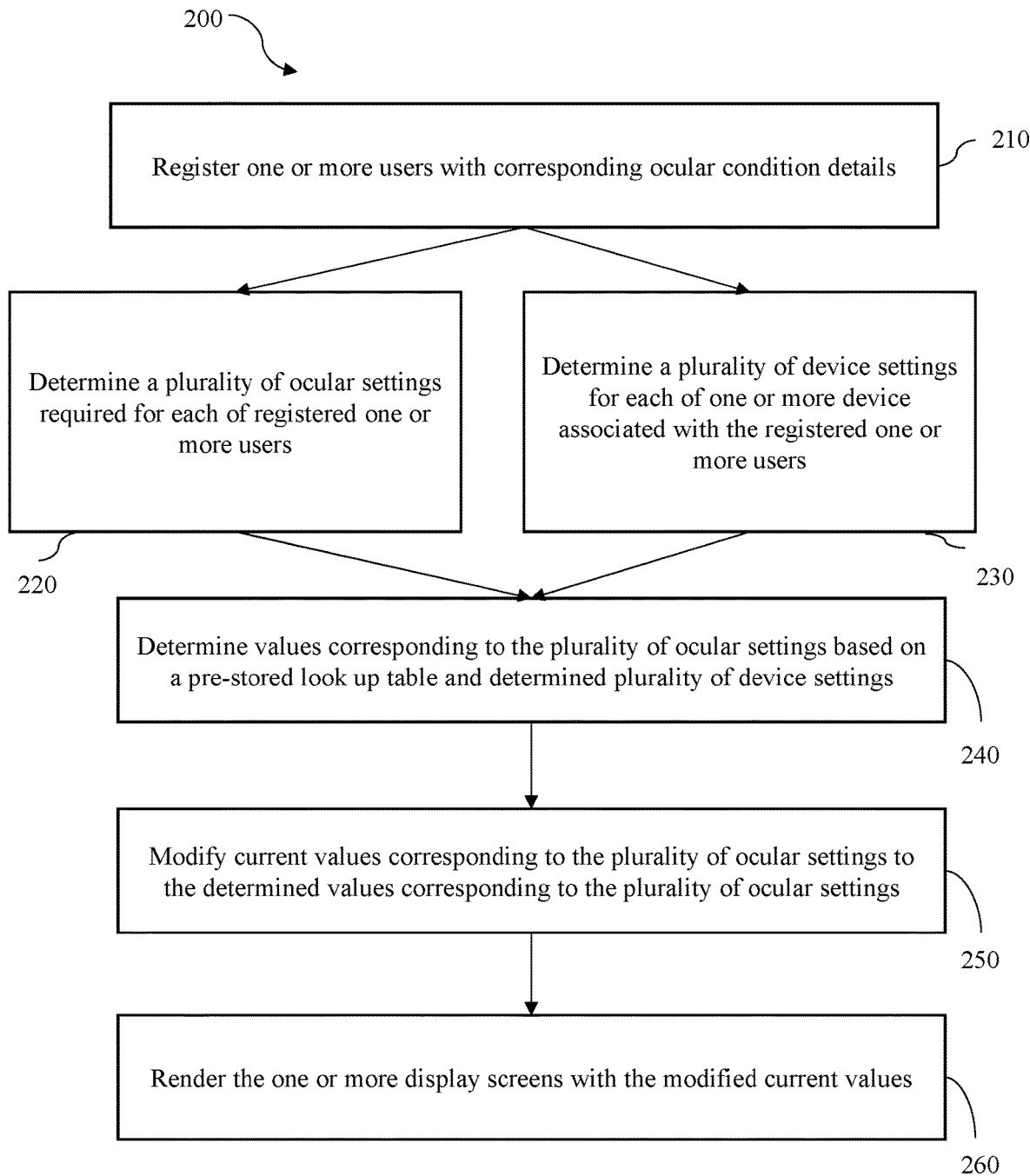
FIG. 4 is a process flowchart illustrating an exemplary method for implementation of ocular assistance in accordance with an embodiment of the present disclosure.

FIG. 4 is a process flowchart illustrating an exemplary method 200 for implementation of ocular assistance in accordance with an embodiment of the present disclosure. At step 210, one or more users are registered with corresponding ocular condition details. In one aspect of the present embodiment, the one or more users are registered with corresponding ocular condition details by an ocular condition registration subsystem 60. In another aspect of the present embodiment, registering the one or more users with corresponding ocular condition details comprises information associated with the at least one of the degree of myopia, the degree of hyperopia, the degree of astigmatism, the degree of presbyopia, and the colour blindness.

At step 220, a plurality of ocular settings required for each of registered one or more users is determined. In one aspect of the present embodiment, the plurality of ocular settings required for each of registered one or more users is determined by an ocular calibration subsystem 70.

At step 230, a plurality of device settings for each of one or more device associated with the registered one or more users are determined. In one aspect of the present embodiment, the plurality of device settings for each of one or more device associated with the registered one or more users is determined by a device configuration identification subsystem 80. In another aspect of the present embodiment, the one or more devices comprises a handheld mobile, a laptop, a desktop and a smart watch.

At step 240, values corresponding to the plurality of ocular settings is determined based on a pre-stored look up table and determined plurality of device settings. In one aspect of the present embodiment, the values corresponding to the plurality of ocular settings are determined based on the pre-stored look up table and determined plurality of device settings by a screen customization subsystem 90.

At step 250, current values corresponding to the plurality of ocular settings is modified to the determined values corresponding to the plurality of ocular settings. In one aspect of the present embodiment, the current values corresponding to the plurality of ocular settings is modified to the determined values corresponding to the plurality of ocular settings by the screen customization subsystem 90.

At step 260, the one or more display screens are rendered with the modified current values. In one aspect of the present embodiment, the one or more display screens are rendered with the modified current values by the screen customization subsystem 90.

The method 200 further includes generating a profile for each of the registered one or more users based on average distance maintained by each of the registered one or more users with respect to the display screen, variations in the distance maintained by each of the registered one or more users in comparison with a predefined distance most suitable for reading, position of head. In another embodiment, the method 200 includes generating a profile for each of the each of registered one or more users based on posture of each of the registered one or more users, ocular condition of the each of the registered one or more users and the computed corrective calibration for each of the registered one or more users.

The method 200 further comprises determining if the ocular settings correspond to colour blindness. In such embodiment, one or more colours present in one or more images or texts are identified and annotated for determined colour blindness.

The system 10 provides ocular assistance to one or more users who are suffering with one or more types of eye condition. In such embodiment, the system 10 modifies or rectifies the screen images or texts for such suffering one or more users. This sets each of the one or more users free to work for long durations without using prescribed spectacles. Further, the system 10 also generates the profile of the each of the one or more users and suggest corrective posture. This helps in solving several physical conditions that arises in lower back, neck, and shoulder portions of the viewer because of wrong posture. It may also help in preventing further aberration in ocular condition of the viewer.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

We claim:

1. A system for ocular assistance, the system comprising:
a hardware processor; and
a memory coupled to the hardware processor, wherein the memory comprises a set of program instructions in the form of a plurality of subsystems, configured to be executed by the hardware processor, wherein the plurality of subsystems comprises:
an ocular condition registration subsystem configured to register one or more users with a plurality of corresponding ocular condition details, wherein the plurality of corresponding ocular condition details relate to
an oculus sinister, and
an oculus dextrus;
an ocular calibration subsystem configured to determine a plurality of ocular settings required for each of registered one or more users through a prestored lookup table, wherein the plurality of ocular settings comprises a plurality of display screen settings comprising pixel size, zoom factor, scale factor, screen resolution, saturation level, contrast level, brightness level and icon arrangement;
a colour detection and annotation subsystem configured to
determine if the plurality of ocular settings correspond to a colour blindness, wherein the colour detection and annotation subsystem is configured to
identify one or more colours present in at least one of image or text when the colour blindness corresponds to the plurality of ocular settings, and
annotate one or more colours present in at least one of image and text when the colour blindness corresponds to the plurality of ocular settings;
a device configuration identification subsystem configured to determine a plurality of device settings for each of one or more device associated with the registered one or more users; and
a screen customization subsystem configured to
determine values corresponding to the plurality of ocular settings based on the pre-stored look up table and the determined plurality of device settings;
modify current values corresponding to the plurality of ocular settings to the determined values corresponding to the plurality of ocular settings; and
render the one or more display screens with the modified current values.

2. The system as claimed in claim 1, wherein the ocular condition details comprise information associated with at least one of degree of myopia, degree of hyperopia, degree of astigmatism, degree of presbyopia, and colour blindness.

3. The system as claimed in claim 1, wherein the one or more devices comprises a handheld mobile, a laptop, a desktop, a head-mounted display device and a smart watch.

4. The system as claimed in claim 1, further comprising a profile generation subsystem configured to generate a profile for each of the each of registered one or more users based on average distance maintained by each of the registered one or more users with respect to the display screen, variations in the distance maintained by each of the registered one or more users in comparison with a predefined distance corresponding to reading, position of head, posture of each of the registered one or more users, ocular condition of the each of the registered one or more users and the computed corrective calibration for each of the registered one or more users.

5. A method for implementation of ocular assistance, the method comprising:
registering, by a processor, one or more users with a plurality of corresponding ocular condition details wherein the plurality of corresponding ocular condition details relate to an oculus sinister, and an oculus dextrus;
determining, by the processor, a plurality of ocular settings required for each of registered one or more users through a prestored lookup table, wherein the plurality of ocular settings comprises a plurality of display screen settings comprising pixel size, zoom factor, scale factor, screen resolution, saturation level, contrast level, brightness level and icon arrangement;
determining, by the processor, if the plurality ocular settings correspond to a colour blindness;
identifying, by the processor, one or more colours present in at least one of image or text when the colour blindness corresponds to the plurality of ocular settings, and
annotating, by the processor, one or more colours present in at least one of image or text when the colour blindness corresponds to the plurality of ocular settings;
determining, by the processor, a plurality of device settings for each of one or more device associated with the registered one or more users;
determining, by the processor, values corresponding to the plurality of ocular settings based on the pre-stored look up table and the determined plurality of device settings;
modifying, by the processor, current values corresponding to the plurality of ocular settings to the determined values corresponding to the plurality of ocular settings; and
rendering, by the processor, the one or more display screens with the modified current values.

6. The method as claimed in claim 5, wherein the ocular condition details comprise information associated with at least one of degree of myopia, degree of hyperopia, degree of astigmatism, degree of presbyopia, and colour blindness.

7. The method as claimed in claim 5, wherein the one or more devices comprises a handheld mobile, a laptop, a desktop, a head-mounted display device and a smart watch.

8. The method as claimed in claim 5, further comprising:
generating a profile for each of the each of registered one or more users based on average distance maintained by each of the registered one or more users with respect to the display screen, variations in the distance maintained by each of the registered one or more users in comparison with a predefined distance corresponding to reading, position of head, posture of each of the registered one or more users, ocular condition of the each of the registered one or more users and the computed corrective calibration for each of the registered one or more users.

* * * * *